United States Patent [19]  [11] Patent Number: 5,290,303
Pingleton et al.  [45] Date of Patent: Mar. 1, 1994

[54] SURGICAL CUTTING INSTRUMENT

[75] Inventors: Edward D. Pingleton; Paul G. Thomson, both of Fillmore, Ind.

[73] Assignee: Vance Products Incorporated D/B/A Cook Urological Incorporated, Spencer, Ind.

[21] Appl. No.: 942,134

[22] Filed: Sep. 8, 1992

Related U.S. Application Data

[63] Continuation of Ser. No. 543,679, Jun. 22, 1990, abandoned.

[51] Int. Cl.$^5$ ............................................. A61B 17/20
[52] U.S. Cl. ...................................................... 606/170
[58] Field of Search ................ 606/159, 170; 604/22, 604/167, 170–180; 128/253, 754, 751, 752

[56] References Cited

U.S. PATENT DOCUMENTS

| | | | |
|---|---|---|---|
| 1,663,761 | 3/1928 | Johnson | 606/159 |
| 3,400,708 | 9/1968 | Scheidt | 128/757 |
| 3,614,953 | 10/1971 | Moss | 606/159 |
| 4,203,444 | 5/1980 | Bonnell et al. | 604/22 |
| 4,246,902 | 1/1981 | Martinez | 606/171 |
| 4,274,414 | 6/1981 | Johnson et al. | 128/305 |
| 4,517,977 | 5/1985 | Frost | 606/170 |
| 4,598,710 | 7/1986 | Kleinberg et al. | 128/751 |
| 4,662,869 | 5/1987 | Wright | 128/752 |
| 4,674,502 | 6/1987 | Imonti | 128/752 |
| 4,729,763 | 3/1988 | Henrie | 606/170 |
| 4,754,755 | 7/1988 | Husted | 606/159 |
| 5,031,634 | 7/1991 | Simon | 128/754 |
| 5,047,008 | 9/1991 | de Juan, Jr. et al. | 128/751 |

FOREIGN PATENT DOCUMENTS 9005493  5/1990  Sweden .................... 604/22

*Primary Examiner*—John D. Yasko
*Assistant Examiner*—Manuel Mendez
*Attorney, Agent, or Firm*—Richard J. Godlewski

[57] ABSTRACT

A surgical cutting instrument is disclosed for percutaneously debulking tissue through an access sheath commonly used in minimally invasive laparoscopic or endoscopic surgical procedures. The cutting instrument includes a inner rotary member tube having a cutting edge at the distal end thereof for cutting and slicing tissue. The distal end of the cutting member tube extends from the distal end of a stationary sheath which prevents tissue from wrapping around the inner cutting member tube. The inner cutting member tube includes a hollow passageway for suctioning and aspirating tissue and fluid through the tube and into a collection chamber or out through a vacuum or suction line attached thereto. The instrument further includes an outer safety shield having a rounded distal end for preventing the puncture of a surgical tissue bag or from unintentionally cutting tissue by the attending physician. The outer shield has a channel across the distal end through the hollow passageway therein for feeding tissue into the cutting edge and controlling the vacuum applied to the tissue. Vacuum or suction control ports are included at the proximal end of the inner cutting member tube and stationary sheath for also controlling the amount of vacuum or suction applied to the tissue. The surgical cutting instrument includes a control handle for grasping by the physician. A removable collection chamber is connected to a coupler connected to the stationary sheath for collecting tissue therein. The inner cutting member tube extends through the collection chamber to a drive motor or to a remotely positioned rotary drive mechanism. A vacuum line is attached to the collection chamber for drawing tissue and fluid through the inner cutting member tube and into the collection chamber.

17 Claims, 3 Drawing Sheets

SURGICAL CUTTING INSTRUMENT

This is a continuation of copending application Ser. No. 07/543,679 filed on Jun. 22, 1990, and now abandoned.

TECHNICAL FIELD

This invention relates to percutaneous surgical cutting instruments and, in particular, surgical instruments for debulking biological tissue.

BACKGROUND OF THE INVENTION

One of the major problems associated with minimally invasive surgery is percutaneously debulking or reducing a large tissue volume such as with a cyst, tumor, or an organ for removal through an access sheath. A number of power-driven, surgical cutting instruments are presently available in which a side port or a partial opening at the distal end of a cutting tube are rotated to shear and aspirate bone and cartilage through a lumen of the instrument. These side ports or partially open-ended cutting instruments are inefficient in debulking large volumes of soft- tissue due to their limited access cutting surfaces, which require an angled or a side approach for cutting. Furthermore, these side port or partially open-ended instruments cannot core soft tissue. This significantly increases the time necessary to debulk and remove tissue through an access sheath. This is particularly applicable in laparoscopic or pelviscopic procedures in which large fibroid cysts must be removed. These power-driven side port or partially open-ended instruments are best suited for cutting cartilage or bone material in arthroscopic procedures, but are very inefficient in debulking and removing large volumes of soft tissue.

Another side port cutting instrument is manually operated and uses a series of opposing jaws that are opened and closed to grasp and shear the tissue. Such a manually-operated device is extremely limited in debulking tissue because of the time required for grasping and cutting each piece of the large tissue volume.

Another problem associated with these side port or partially open-ended instruments are the complex angles that are required for the cutting edges. Not only do these complex cutting angle instruments have limited access, but also provide limited control or directionality with respect to slicing or cutting soft tissue.

SUMMARY OF THE INVENTION

The foregoing problems are solved and a technical advantage is achieved by a surgical cutting instrument in which an open-ended rotary cutting edge positioned about the distal end of an inner elongated member extends beyond the distal end of a stationary outer sheath. The stationary sheath provides a protective guard for the inner member by limiting the lateral contact of the inner member with tissue, which advantageously prevents the wrapping of tissue around the inner rotary cutting member. The stationary sheath not only prevents tissue from wrapping around the rotary cutting member, but also prevents unwanted tearing or binding of the, tissue around the inner cutting member. Wrapping tissue around the inner cutting member also severely limits the control and directionality of the cutting member through the tissue being debulked.

The rotary cutting edge extends circumferentially about the distal end of the inner member, thereby providing continual and head-on controlled cutting or debulking of the tissue. Such a configuration advantageously provides direct cutting or slicing of the tissue while maintaining precise control of the cutting operation.

The cutting edge of the inner rotating tube is radiused to cut soft tissue but yet not cut a surgical tissue bag, which may be brought in contact with the inner rotary cutting member.

Another outer safety shield is positioned about the inner cutting member and the stationary sheath and includes a rounded distal end, which further prevents puncturing of a tissue bag or unintended cutting of tissue. Laterally located about the distal end of the safety shield tube is an access channel through the passageway thereof for accepting tissue and guiding the tissue against the cutting edge of the inner rotary cutting member. This advantageously acts as a jaw for feeding the tissue into the cutting edge for cutting large portions of tissue. This variable size access channel also acts as a valve to control aspiration of fluid and tissue through the hollow passageway of the inner cutting member. Vacuum or suction control ports at the proximal end of the inner member and intermediately positioned stationary sheath also regulate the amount of vacuum or suction that is applied to the passageway of the inner cutting member for aspirating tissue or fluid therethrough.

The outer safety shield longitudinally slides along the stationary sheath to close and open the suction control ports of the inner member and the sheath for controlling the amount of vacuum or suction applied for aspirating tissue or fluid. The outer safety shield is also longitudinally extendable and withdrawable for controlling the size of the side access channel.

The outer shield includes a radial control arm attached to the proximal end of the shield for longitudinally sliding the shield with respect to the inner cutting member and stationary sheath and controlling the size of the side access channel and suction control ports.

The surgical cutting instrument also includes a collection chamber and an evacuation port for connecting a vacuum line thereto for aspirating tissue and fluid. The instrument further includes a rotary drive mechanism and coupler for rotating said inner member. A handle at the proximal end of the cutting instrument allows directional control of the instrument along with providing manual control of the instrument and the outer shield.

DETAILED DESCRIPTION

Figure 1:
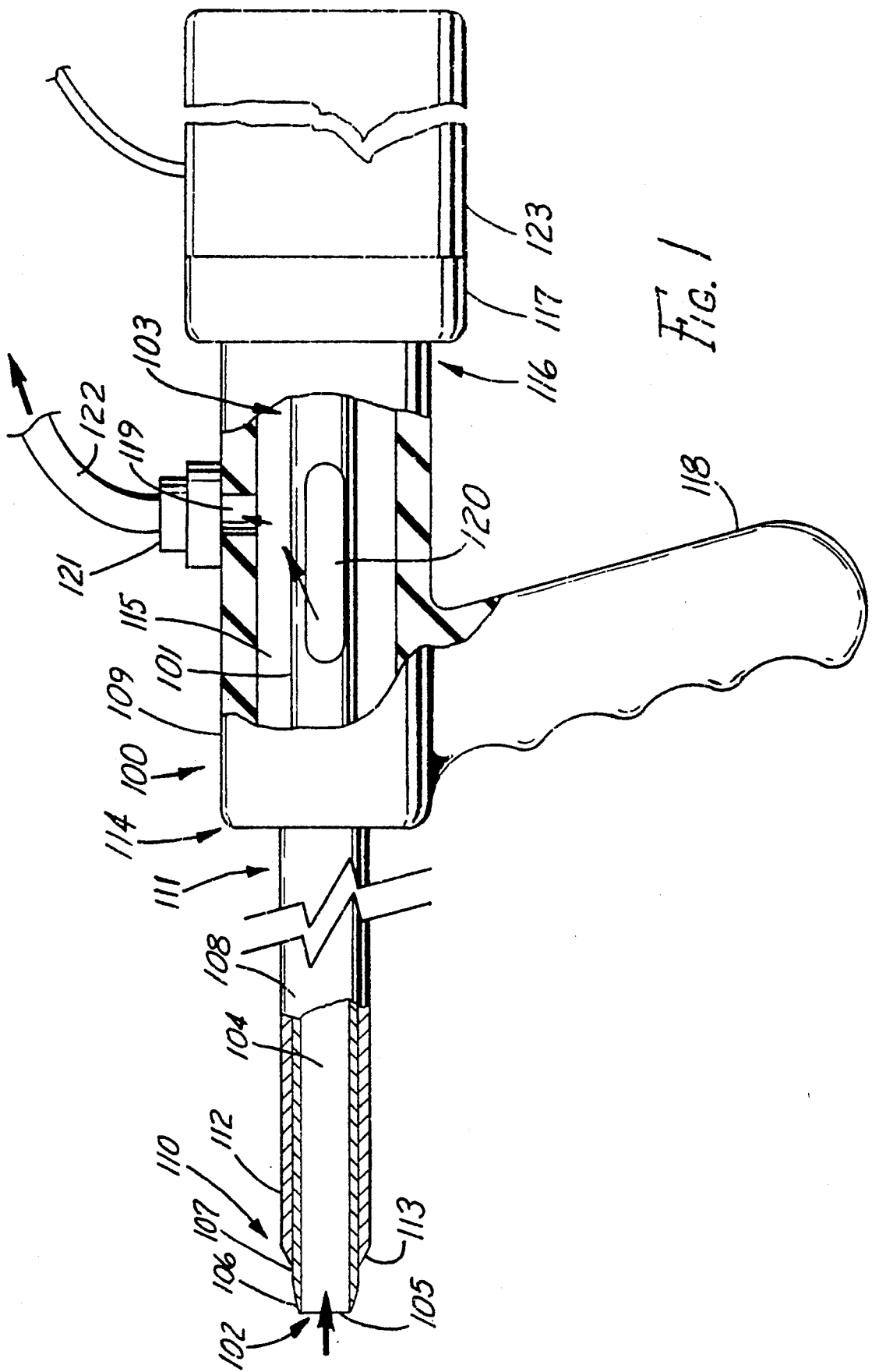
FIG. 1 depicts an illustrative surgical cutting instrument of the present invention.

Depicted in FIG. 1 is an illustrative surgical cutting instrument 100 for percutaneously debulking and cutting tissue through an access sheath that is commonly utilized in minimally invasive surgery. A trocar sheath is normally pushed through the skin and subcutaneous tissue layers into a cavity of the patient during, for example, an endoscopic or laparoscopic procedure. The cutting instrument is inserted through the sheath or into a percutaneously positioned surgical tissue bag for debulking or reducing large tissue volumes such as cysts, tumors, organs or the like. A preferred surgical tissue bag is disclosed in a U.S. patent application of one of the present inventors and filed concurrently herewith.

The cutting instrument comprise's an inner elongated member tube 101 having a distal end 102, a proximal end 103, and a hollow passageway 104 extending longitudinally therebetween. Positioned at the distal end of the inner member tube is a rotary cutting edge 105 that is circumferentially positioned thereabout. The cutting edge includes radius 106 extending from the hollow passageway to an outer surface 107 of the inner member tube. The radiused edge reduces the possibility of puncturing a surgical tissue bag or unintentionally cutting tissue. Surrounding the rotary cutting tube is elongated stationary sheath 108 connected to coupler 109. The stationary sheath has a distal end 110, a proximal end 111, and a hollow passageway 112 positioned longitudinally therebetween. Distal end 112 includes a bevel 113 extending circumferentially therearound for preventing the tearing or ripping of tissue coming in contact therewith. By way of example, inner cutting member tube is a stainless steel tube having a 0.300" diameter with a wall thickness of 0.010". The stationary sheath is also a stainless steel tube having a 0.330" outside diameter with a 0.010" wall thickness. The lengths of the inner cutting member tube and the stationary sheath range in length preferably from 5-10 cm.

The proximal end 111 of stationary sheath 108 is connected to the distal end 114 of coupler 109. A hollow passageway 115 extends through the coupler to the proximal end 116 thereof where rotary drive mechanism 117 is connected thereto. By way of example, rotary drive mechanism 117 includes a well-known DC electric motor 123 connected to the proximal end 103 of rotary inner member tube 101. Alternatively, drive mechanism 123 may include a casing and well-known bearings for applying air to a turbine also positioned at the proximal end of the inner cutting member tube. Other well-known means of providing a rotary motion to the inner cutting member are also contemplated. A handle 118 extends radially from the coupler to provide manual control of the entire cutting instrument by the attending physician. An evacuation port 119 extends radially from hollow coupler passageway 115 for suctioning tissue and other fluid from side proximal evacuation port 120 of inner cutting member tube 101. A well-known connector 121 provides means for fastening a vacuum line or suction tube 122 to coupler 109.

As previously suggested, the inner cutting member tube extends through stationary sheath 108 with the proximal end 103 extending through the hollow passageway of the coupler for connection to rotary drive mechanism 117.

Figure 2:
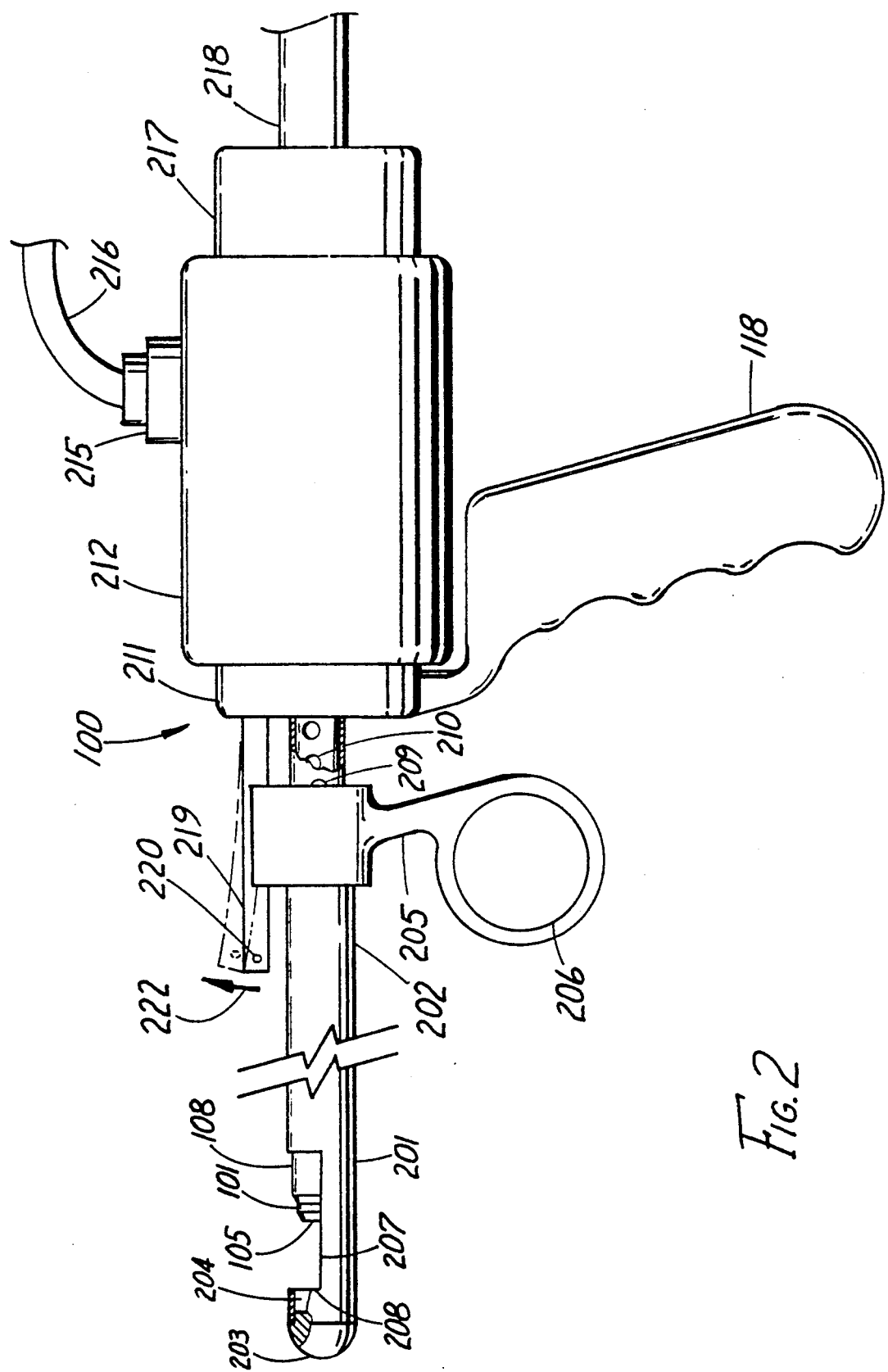
FIG. 2 depicts the surgical cutting instrument of FIG. 1 modified to receive an outer shield for containing the inner cutting member and stationary sheath of FIG. 1.
Figure 3:
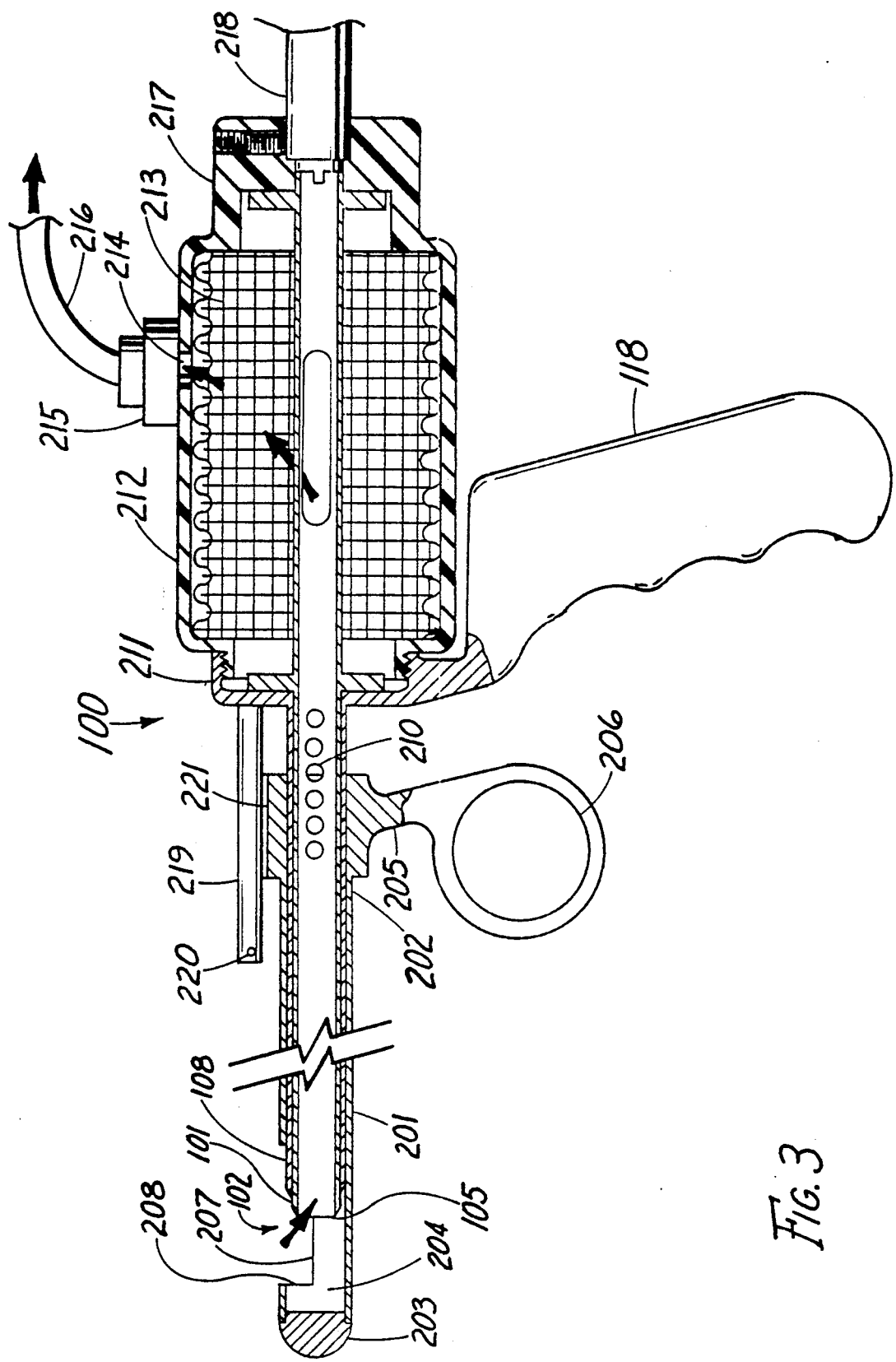
FIG. 3 is a cross-sectional view of the surgical cutting instrument of FIG. 2.

Depicted in FIG. 2 is a side view and in FIG. 3 a partial cross-sectional view of a modified embodiment of surgical cutting instrument 100 of FIG. 1 with an outer safety shield 201 positioned about stationary sheath 108 and inner cutting member tube 101. Outer safety shield 201 includes a proximal end 202, a rounded distal end 203, and a hollow passageway 204 positioned and extending longitudinally therebetween. The shield is sized for inserting the stationary sheath and the inner cutting member tube within passageway 204. By way of example, the outer shield comprises a stainless steel tube having a 0.340" outside diameter with a wall thickness of 0.015". The distal end 203 of the outer shield is rounded to prevent unintentional cutting of tissue and puncturing the surgical tissue bag should such be utilized in the surgical procedure.

Extending radially from the proximal end is a control arm 205 having an eyelet ring 206 at the proximal end thereof for slidably controlling the position of the outer shield with respect to stationary sheath 108 and inner cutting member tube 101. The attending physician typically inserts his index finger therein while the rest of the hand grasps control handle 118.

Positioned about the distal end 203 of the outer shield is access channel 207 that extends laterally across the shield tube and through hollow passageway 204. Face edge 208 of the channel acts as a jaw for grasping tissue and feeding it into cutting edge 105 of the inner cutting member tube. In this modified embodiment, distal end 102 of the inner cutting member tube is beveled to provide a sharper cutting edge 105. Control eyelet ring 206 is longitudinally moved by the physician to cause face edge 208 of the channel to engage and draw the tissue into the cutting edge of the inner cutting member tube.

A plurality of vacuum control ports 209 are positioned longitudinally along the length of stationary sheath 108. A plurality of vacuum access ports 210 are correspondingly positioned with respect to access ports 209 of the stationary sheath to control the amount of vacuum applied to the distal end of the inner cutting member tube. As the outer shield 201 is longitudinally moved along stationary sheath 108, the vacuum control access ports are either opened or covered up to allow respectively more or less suction to be applied to the distal end of the inner cutting member tube.

As depicted in FIGS. 2 and 3, coupler 211 has been modified to receive a detachable tissue collection chamber 212. Handle 118 is fixedly attached to coupler 211 as is stationary sheath 108. The collection chamber is of a cylindrical form including a cylindrical collection screen 213 for collecting tissue as vacuum is applied via evacuation port 214, vacuum connector 215, and vacuum tube 216. Vacuum tube 216 is connected to a source of suctioning vacuum, which is readily available in most surgical suites. The inner cutting member tube extends longitudinally through the collection chamber to rotary drive mechanism 217 which is part of the proximal end of the collection chamber. The proximal end of the inner rotary cutting member tube is connected to a remote source of rotary power via rotary power line 218. Means for positioning the inner cutting member tube within the collection chamber using two bearing flanges and a slotted end are well-known in the art and may be readily modified by one skilled in the art to accept any number of different types of rotary drive mechanisms. The rotary drive mechanism may include a remote source of power as indicated in this particular example or may be integrally incorporated into the cutting instrument as was described with respect to FIG. 1.

Extending longitudinally from coupler 211 is elongated stop arm 219 having a cross member 220 positioned at the distal end thereof. The built-up distal end of radial control arm 205 includes a longitudinal slot or channel 221 formed therein for slidably receiving stop arm 219. Cross member 220 limits the longitudinal motion of the outer shield when control arm 205 engages cross member 220. The distal end of the control arm is moveable as shown by arrow 222 to remove the outer shield for cleaning.

It is to be understood that the above-described surgical cutting instrument is merely an illustrative embodiment of the principles of this invention and that other cutting instruments may be devised by those skilled in the art without departing from the spirit and scope of this invention. In particular, the distal end of the cutting instrument may be devised to include serrated teeth or a modified cutting edge for providing any number of different cutting or slicing actions. The rounded distal end of the outer shield may be devised to include a series of rounded wires to permit penetration through soft tissue to permit cutting and slicing by the inner cutting member tube. Such a wire cage arrangement would also prevent puncture of a surgical tissue bag should one be desired to be used by the physician.

What is claimed is:

1. A surgical cutting instrument comprising:
   an elongated sheath having a distal end, a proximal end, and a hollow passageway positioned longitudinally therebetween, said sheath also having an outer surface including a bevel extending longitudinally from said distal end of said sheath; and
   a rigid inner elongated member rotatably positioned within and extending through said hollow passageway of said sheath, said member having an open distal end extending beyond said distal end of said sheath, a proximal end connectable to a rotary drive mechanism, and a hollow passageway extending longitudinally therethrough from said open distal end thereof for removing tissue, said member being in rotational contact with said elongated sheath about said distal and proximal ends thereof, said open distal end of said inner elongated member including a rotary cutting edge positioned circumferentially around said hollow passageway and said open distal end of said inner member for cutting through tissue when said member is rotated, said inner member having an outer surface including a predetermined radius extending longitudinally from said cutting edge and said open distal end.

2. The instrument of claim 1 wherein said inner member includes a side port positioned about said proximal end and extending from said hollow passageway thereof and opening exterior to said member.

3. The instrument of claim 1 further comprising said rotary drive mechanism.

4. The instrument of claim 1 further comprising an outer elongated shield having a proximal end, a distal end, and a hollow passageway positioned longitudinally therebetween and sized for insertion of said sheath and said inner member therein, said distal end of said shield having a predetermined puncture-resistant shape, said shield having a recessed channel positioned about said distal end of said shield, extending laterally across said hollow passageway of said shield, and opening exterior to an outer surface of said shield, said recessed channel having oppositely facing edges, at least one of said oppositely facing edges for feeding tissue into said cutting edge.

5. The instrument of claim 4 wherein said outer shield includes a control arm extending radially from said proximal end thereof.

6. The instrument of claim 4 wherein said elongated sheath includes a first plurality of ports extending through a wall thereof and positioned longitudinally about said proximal end thereof and wherein said inner member includes a second plurality of ports extending through a wall thereof, periodically communicating with said first plurality of ports when said inner member is rotated, and positioned longitudinally about said proximal end thereof.

7. The instrument of claim 1 further comprising a coupler having a distal end connected about said proximal end of said elongated sheath and a proximal end connectable to said rotary drive mechanism and wherein said coupler includes a tissue collection chamber communicating with said passageway of said inner elongated member.

8. The instrument of claim 5 wherein said outer shield includes a hub attached about said proximal end thereof and an elongated stop member extending from said hub longitudinally alongside said outer shield.

9. The instrument of claim 8 wherein said control arm includes a channel therein for insertion of said elongated stop member.

10. A surgical cutting instrument comprising;
    an outer shield having a proximal end, a distal end, a hollow passageway extending longitudinally between said ends, and a recessed channel positioned about said distal end of said shield, extending laterally across said passageway, and opening exterior to an outer surface of said shield, said recessed channel having oppositely facing edges, said distal end having a predetermined puncture-resistant shape;
    an elongated sheath having a distal end, a proximal end, and a hollow passageway therebetween and sized for insertion into said passageway of said shield, said sheath also having an outer surface including a bevel extending longitudinally from said distal end of said sheath; and
    an inner elongated member rotatably positioned within said hollow passageway of said elongated sheath, said distal end of said member having a distal end positioned beyond said distal end of said sheath and including a rotary cutting edge positioned circumferentially thereabout for cutting through tissue, at least one of said oppositely facing edges of said recessed channel for feeding tissue into said cutting edge.

11. The instrument of claim 10 further comprising a tissue collection chamber connected to said proximal end of said sheath, said inner member having a hollow passageway extending longitudinally therethrough for removing tissue and further having an evacuation port extending from said passageway thereof and opening into said collection chamber.

12. The instrument of claim 11 wherein each of said inner member and said sheath includes a plurality of control ports extending therealong longitudinally and from said passageway thereof and opening exterior to an outside surface thereof, the plurality of control ports of said inner member and said sheath periodically communicating with each other when said inner member is rotated.

13. The instrument of claim 12 wherein said outer shield includes a control arm extending radially from said proximal end thereof.

14. The instrument of claim 13 further comprising a rotary drive mechanism connected to said inner member.

15. The instrument of claim 14 wherein said tissue collection chamber includes an evacuation port.

16. The instrument of claim 15 further comprising a stop arm extending longitudinally therealong and a lateral cross member positioned about a distal end of said stop arm for limiting longitudinal movement of said shield with respect to said sheath.

17. A surgical cutting instrument comprising:
- an outer shield having a proximal end, a distal end, and a hollow passageway extending longitudinally therebetween, said distal end having a predetermined puncture-resistant shape and a recessed access channel positioned thereabout, extending laterally across said passageway and opening exterior to an outer surface of said shield, said recessed channel having oppositely facing edges, said outer shield further including a control arm extending radially from said proximal end thereof;
- an elongated sheath having a distal end, a proximal end, and a hollow passageway therebetween and sized for insertion into said passageway of said shield;
- a control handle connected to said elongated sheath and extending radially from said sheath;
- an inner elongated member rotatably positioned within said hollow passageway of said elongated sheath, said member having a distal end extending beyond said distal end of said sheath, said distal end of said member including a rotary cutting edge positioned circumferentially thereabout, at least one of said oppositely facing edges of said recessed channel for feeding tissue into said cutting edge;
- said inner member including a first plurality of control ports positioned longitudinally therealong, extending from said passageway thereof, and opening exterior to an outside surface thereof;
- said sheath including a second plurality of control ports positioned longitudinally therealong, periodically communicating with said first plurality of ports when said inner member is rotated, extending from said passageway thereof, and opening exterior to an outside surface thereof;
- a tissue collection chamber removably connected to said control handle and said proximal end of said sheath, said inner member extending into said chamber and having an evacuation port extending from said passageway thereof and opening into said collection chamber, said collection chamber including an evacuation port and a rotary drive mechanism connected to said proximal end thereof, said rotary drive mechanism being removably connected to said inner elongated member; and
- a stop arm connected to said control handle and extending longitudinally along said outer shield and having a cross member positioned about a distal end thereof for limiting longitudinal movement of said outer shield with respect to said sheath.

* * * * *